(12) United States Patent
Freeman et al.

(10) Patent No.: US 8,337,837 B2
(45) Date of Patent: *Dec. 25, 2012

(54) STABLE ENZYMATIC PREPARATIONS AND METHODS OF USE THEREOF

(75) Inventors: Amihay Freeman, Ben-Shemen (IL); Noa Hadar, Kibbutz Givat Brenner (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/350,846

(22) Filed: Jan. 16, 2012

(65) Prior Publication Data

US 2012/0114631 A1 May 10, 2012

Related U.S. Application Data

(63) Continuation of application No. 12/087,108, filed as application No. PCT/IL2006/001492 on Dec. 27, 2006, now Pat. No. 8,197,808.

(60) Provisional application No. 60/753,400, filed on Dec. 27, 2005.

(51) Int. Cl.
*A61K 38/46* (2006.01)

(52) U.S. Cl. .................................... 424/94.65

(58) Field of Classification Search ................. 424/94.65
See application file for complete search history.

(56) References Cited

U.S. PATENT DOCUMENTS

| 3,539,451 A | 11/1970 | Heinicke |
| 4,307,081 A | 12/1981 | Klein et al. |
| 4,715,899 A | 12/1987 | Chanda et al. |
| 6,692,726 B1 | 2/2004 | Morgan et al. |
| 2009/0220483 A1 | 9/2009 | Freeman et al. |
| 2012/0114631 A1 | 5/2012 | Freeman et al. |

FOREIGN PATENT DOCUMENTS

| EP | 0472001 | 2/1992 |
| GB | 913203 | 12/1962 |
| JP | 04-049299 | 2/1992 |
| JP | 07-298850 | 11/1995 |
| JP | 2005-515180 | 5/2005 |
| WO | WO 03/041680 | 5/2003 |
| WO | WO 2005/034892 | 4/2005 |
| WO | WO 2005/070480 | 8/2005 |
| WO | WO 2007/074454 | 7/2007 |

OTHER PUBLICATIONS

International Preliminary Report on Patentability Dated Jul. 10, 2008 From the International Bureau of WIPO Re.: Application No. PCT/IL2006/001492.
International Search Report and the Written Opinion Dated Jul. 17, 2007 From the International Searching Authority Re.: Application No. PCT/IL2006/001492.
Official Action Dated Nov. 2, 2011 From the US Patent and Trademark Office Re. U.S. Appl. No. 12/087,108.
Response Dated Feb. 25, 2010 to Communication Pursuant to Article 94(3) EPC of Aug. 18, 2009 From the European Patent Office Re.: Application No. 06821673.8.
Arnon "The Cysteine Proteases. Papain", Methods of Enzymology, 19(Art.14): 226-244, 1970.
Sigma-Aldrich "Papain. Enzyme Explorer", Sigma-Aldrich Co. LLC, Retrieved From the Internet, 2011.
Notice of Reason for Rejection Dated Mar. 13, 2012 From the Japanese Patent Office Re. Application No. 2008-548072.

*Primary Examiner* — Karen Cochrane Carlson

(57) ABSTRACT

The present invention relates to stable concentrated enzymatic compositions suitable for storage under ambient conditions, while maintaining their intended enzymatic activity. The invention further relate to kits comprising concentrated enzymatic compositions, methods for preparing debriding solutions from said concentrated enzymatic compositions and methods of using the diluted debriding solutions.

30 Claims, 8 Drawing Sheets

STABLE ENZYMATIC PREPARATIONS AND METHODS OF USE THEREOF

RELATED APPLICATIONS

This application is a continuation of U.S. patent application Ser. No. 12/087,108 filed on Feb. 10, 2009, which is a National Phase of PCT Patent Application No. PCT/IL2006/001492 having International filing date of Dec. 27, 2006, which claims the benefit of priority of U.S. Provisional Patent Application No. 60/753,400 filed on Dec. 27, 2005. The contents of the above Applications are all incorporated herein by reference.

FIELD OF THE INVENTION

The present invention relates to stable concentrated enzymatic compositions suitable for storage under ambient conditions, while maintaining their intended enzymatic activity. The invention further relate to kits comprising concentrated enzymatic compositions, methods for preparing debriding solutions from said concentrated enzymatic compositions and methods of using the diluted debriding solutions.

BACKGROUND OF THE INVENTION

Patients suffering from chronic ulcers and particularly diabetic ulcers are at high risk for local and systemic infections. In the frequent events of leg and foot ulcers, these patients are also at risk of structural foot deformity, limited joint mobility and amputation. Treatments for infected ulcers include glycemic control, systemic antibiotics and meticulous wound care, mainly debridement of necrotic tissue. Debridement is typically attempted by surgical methods, however, non-surgical methods including use of debriding enzymes, have been devised to avoid the blood loss and pain inherent in surgery. Furthermore, enzymatic debridement does not require exposure of the injured patient to additional trauma related to the surgical procedure and yet provides an immediate and a fast resolution of the emergency medical conditions associated with ulcers.

Debriding enzymes are also useful for treating severe skin problems, such as eczema, psoriasis and the like, and less severe skin conditions, such as wrinkles, acne and dry skin, as disclosed for example in U.S. Pat. Nos. 4,524,136; 5,439,935; 5,441,740; 5,554,366; 5,853,705 and 6,780,444. Commercial products comprising such enzymes are also available, e.g. Accuzyme® (papain) and Granulex® (trypsin), the application of which is limited for debridement of wounds.

U.S. Pat. Nos. 4,197,291; 4,226,854; 4,307,081; 4,329,430 and 5,830,739 disclose hydrolytic enzymes derived from the pineapple plant and composition comprising same. US Patent Application No. 2003/0026794 discloses methods for treating skin conditions using at least one enzyme that affects one or more particular layers of skin. The aforementioned enzymatic preparations posses limited shelf life under standard storing conditions, such as storage at room temperature.

Enzymatic compositions may be stabilized by moieties that inhibit lose of enzymatic activity during storage. For example, U.S. Pat. No. 6,692,726 discloses stable oral compositions comprising enzymes, cetyl pyridinum chloride and a reducing agent which confer stability to the compositions. Typically, such additives are suitable only for particular enzymes and moreover to particular uses of said enzymes.

Methods and apparatus for applying enzymatic composition onto a wound are taught in WO03/011369, US 2004/0186421 and WO2005/070480 of the inventor of the present invention, all of which are incorporated in their entirety by reference, as is fully set forth herein. These applications disclose apparatus for continuous streaming therapeutic solutions, particularly solutions comprising proteases as the active ingredient, over a wound such as an ulcer.

It was further shown by the inventor of the present invention that applying a stream of active proteolytic enzyme for a few hours, through and over the wound area provides an effective debridement (Freeman et al., *Wound* 16:201-205, June 2004). Similar treatment with a buffer solution devoid of enzymes was found to be ineffective. Furthermore, treatment with a static (non-flowing) composition of enzymes for a similar time period had no effect.

There is an unmet need for enzymatic compositions comprising debriding enzymes and having long shelf life while maintaining effective debriding activity. Advantageously, such compositions should be easy to use and thus can be applied by any user and not necessarily by a health-care professional.

SUMMARY OF THE INVENTION

The present invention provides stable compositions comprising proteolytic enzymes, particularly thiol proteases, and more particularly papain, kits comprising same and methods for enzymatic debridement using said compositions. The compositions of the present invention are convenient for extemporaneous dilution and do not require assistance of a health-care professional for preparation and/or for topical application thereof. The kit of the invention comprises separate components that form the debriding compositions by a simple mixing step.

The present invention is based in part on the unexpected discovery that an active debriding solution can be prepared extemporaneously from a concentrate comprising a concentrated papain solution, a concentrated buffer solution, a concentrated thiol compound and a suitable diluting solution, all of which are maintained in storage for months before being admixed to compose the debriding solution. Surprisingly, even after long periods of storage, the activity of the enzymes stored in the compositions of the present invention is completely, or at least mostly, reestablished upon dilution. Moreover, reconstitution from storage to an active form is straightforward and can be carried out by the patient or any other person who is not necessarily a health-care professional. Unexpectedly, said concentrate remains clear, namely, is devoid of particulate matter, for prolonged periods of storage.

According to one aspect, the present invention provides a composition comprising a non-active stable concentrate of a thiol-protease comprising at least 20 mg/ml of the thiol-protease and further comprising at least one osmotic agent, wherein said thiol-protease upon activation possesses proteolytic activity within the range of 5,000 to 50,000 USP units/mg, wherein one USP unit of papain activity is that which releases an equivalent of 1 mg of tyrosine from a casein substrate solution as described in the United States Pharmacopeia reference guide.

According to one embodiment, the thiol protease is selected from the group consisting of: cysteine proteases derived from plants, including but not limited to, papain, bromelain and ficin. According to a current embodiment, the thiol protease is papain.

It is to be understood explicitly that the scope of the present invention encompasses homologs, analogs, variants and derivatives of papain, with the stipulation that these homologs, analogs, variants and derivatives must preserve the capacity of performing proteolysis and particularly of carrying out debridement of necrotic tissue in wounds, or elimination of the dead cells building up at the surface of the skin (cosmetic peeling), after being stored in a non-active form for long time periods according to the principles of the present invention.

According to another embodiment, the concentration of the thiol-protease is within the range of 25 to 45 mg/ml.

According to yet another embodiment, the non-active concentrate is devoid of particulate matter.

According to yet another embodiment, the at least one osmotic agent is selected from the group consisting of: sodium chloride, glycerol, mannitol, dextran, polyethylene glycol (PEG) and combinations thereof. According to yet another embodiment, the at least one osmotic agent is sodium chloride at a concentration of at least 1% w/v. According to yet another embodiment, the debriding composition comprises at least 3% w/v sodium chloride. According to another embodiment, the debriding composition comprises at least 5% w/v sodium chloride. According to yet another embodiment, the debriding composition comprises glycerol and sodium chloride, wherein the concentration of glycerol is at most 30% v/v and the concentration of sodium chloride is at most 18% w/v. According to yet another embodiment, the at least one osmotic agent is glycerol in a concentration of at most 20% v/v.

According to yet another embodiment, the non-active concentrate is stable upon storage for at least one week, preferably at least one month, more preferably at least 6 months, at ambient temperatures prior to activation, wherein upon activation said thiol-protease possesses proteolytic activity within the range of 5,000 to 50,000 USP units/mg. According to yet another embodiment, the non-active concentrate is stable upon storage for at least one week, preferably at least one month, more preferably at least 6 months, in a temperature within the range of 4-10° C., wherein said thiol-protease upon activation possesses proteolytic activity within the range of 5,000 to 50,000 USP units/mg.

According to yet another embodiment, the composition further comprises a buffer, selected from the group consisting of: N-(2-Acetamido)-2-iminodiacetic acid buffer, acetate buffer, succinate buffer, maleate buffer, citrate buffer, MES buffer and combinations thereof, preferably acetate solution.

According to yet another embodiment, the pH of the concentrated papain solution is within the range of 3-6 pH units, preferably within the range of pH 4-5.

According to yet another embodiment, the composition is isotonic. According to yet another embodiment, the composition is hypertonic.

According to yet another embodiment, the composition is a dry concentrate.

According to another embodiment, the present invention provides a debriding solution comprising the concentrate of the invention diluted in at least one diluting solution, the at least one diluting solution comprising at least one reducing agent, buffer, and at least one chelating agent, wherein said thiol-protease possesses proteolytic activity within the range of 5,000 to 50,000 USP units/mg and wherein the debriding solution has a physiological pH.

According to yet another embodiment, the debriding solution exhibits debriding activity for at least 6 hours. According to yet another embodiment, the debriding solution exhibits debriding activity for at least 12 hours. According to yet another embodiment, the debriding solution exhibits debriding activity following storage for at least 6 hours at 4-10° C. According to yet another embodiment, the debriding solution exhibits debriding activity following storage for at least 12 hours at 4-10° C.

According to yet another embodiment, the at least one reducing agent is a thiol compound selected from the group consisting of: sulfide, cystamine, gluthatione, N-acetyl cysteine, cysteine and cysteine hydrochloride. According to a preferred embodiment, the thiol compound is cysteine hydrochloride.

According to yet another embodiment, the buffer is selected from the group consisting of: tris hydroxymethylaminoethane (Tris) buffer, Hepes buffer, lysine buffer, glycine buffer, MOPS buffer, imidazole buffer and MES buffer. According to a preferred embodiment, the buffer is a Tris buffer.

According to yet another embodiment, the debriding composition is isotonic. According to yet another embodiment, the debriding composition is hypertonic.

According to yet another embodiment, the pH of the debriding composition is within the range of pH 7 to 7.6, preferably, pH 7.2 to 7.6.

According to yet another embodiment, the at least one chelating agent is selected from the group consisting of: ethylenediaminetetracetic acid (EDTA), ethylene bis-(oxyethylene nitro) tetraacetic acid (EGTA) and ethylene dinitrilotetraacetic acid (Titriplex III).

According to another aspect, the present invention provides a kit for preparing a debriding composition, the kit comprises a first component comprising a non-active concentrate of a thiol-protease comprising at least 20 mg/ml of the thiol-protease, and optionally comprising at least one osmotic agent; a second component comprising a concentrated solution of at least one reducing agent; and a third component being a concentrated buffer solution comprising at least one buffering agent and at least one chelating agent, wherein mixing said first, second and third components in at least one diluting solution provides a debriding solution having a physiological pH and wherein said thiol-protease upon activation possesses proteolytic activity within the range of 5,000 to 50,000 USP units/mg.

According to one embodiment, the concentration of the thiol-protease in the first component is within the range of 25 to 45 mg/ml.

According to another embodiment, the thiol protease is selected from the group consisting of: cysteine proteases derived from plants, including but not limited to, papain, bromelain and ficin. According to a current embodiment, the thiol protease is papain.

According to yet another embodiment, the first component is a solution having a pH within the range of pH 3-6, preferably a pH within the range of pH 4-5. According to another embodiment, said first component comprises a buffer capable of maintaining an acidic pH, wherein the buffer is selected from the group consisting of: acetate buffer, succinate buffer, maleate buffer, citrate buffer, MES buffer and combinations thereof. According to a preferred embodiment, the buffer is acetate buffer.

According to another embodiment, the first component is stable upon storage for at least one week, preferably at least one month, more preferably at least 6 months, at ambient temperatures, prior to activation. According to yet another embodiment, the first component is stable upon storage for at least a week, preferably at least a month, more preferably at least 6 months, in a temperature within the range of 4-10° C., prior to activation.

According to yet another embodiment, the at least one reducing agent is a thiol compound selected from the group consisting of: sulfide, cystamine, gluthatione, N-acetyl cysteine, cysteine and cysteine hydrochloride. According to a preferred embodiment, the thiol compound is cysteine hydrochloride. According to yet another embodiment, the pH of the second component is within the range of pH 1 to 4. According to another embodiment, the pH of the second component is within the range of pH 1 to 2.

According to yet another embodiment, the third component comprises a buffering agent selected from the group consisting of: tris hydroxymethylaminoethane (Tris) buffer, Hepes buffer, lysine buffer, glycine buffer, MOPS buffer, imidazole buffer and MES buffer. According to a preferred embodiment, the third component comprises a Tris buffer. According to a particular embodiment, upon dilution with the first, second and third components and the at least one diluting solution, the buffering agent maintains a pH within the range of physiological pH. According to one embodiment, the physiological pH is within the range of pH 7 to 7.6, preferably, pH 7.2 to 7.6.

According to yet another embodiment, upon dilution with the first, second and third components and the at least one diluting solution, a diluted solution having a proteolytic activity within the range of 5,000 to 50,000 USP units/mg is obtained. According to yet another embodiment, the diluted solution is isotonic. According to yet another embodiment, the diluted solution is hypertonic.

According to yet another embodiment, the at least one chelating agent is selected from the group consisting of: ethylenediaminetetracetic acid (EDTA), ethylene bis-(oxyethylene nitro) tetraacetic acid (EGTA) and ethylene dinitrilotetraacetic acid (Titriplex III).

According to yet another embodiment, the at least one diluting solution comprises a solution selected from the group consisting of: saline, hyperosmolaric saline solution and saline solution comprising at least one osmotic agent.

According to yet another embodiment, the hyperosmolaric saline comprises at least 1% w/v sodium chloride, preferably at least 3% w/v sodium chloride. According to another embodiment, the hyperosmolaric saline comprises at least 5% w/v sodium chloride. According to yet another embodiment, the at least one osmotic agent is selected from the group consisting of: sodium chloride, glycerol, mannitol, dextran, PEG and combinations thereof. According to yet another embodiment hyperosmolaric saline comprises glycerol and sodium chloride, wherein the concentration of glycerol is at most 30% v/v and the concentration of sodium chloride is at most 18% w/v.

According to yet another embodiment, the content of the at least one osmotic agent is at most 10% v/v. According to yet another embodiment, the content of at least one osmotic agent is at most 20% v/v.

According to one embodiment, the volume ratio between each component of the kit and the volume of the debriding solution is at least 1:10. According to another embodiment, said volume ratio is at least 1:20.

According to an alternative embodiment, the first component further comprises an inhibitor being capable of inhibiting the debriding activity of papain in a reversible manner. According to another alternative embodiment, the at least one inhibitor is selected from the group consisting of: heavy metal, a carbonyl reagent, an aldyehyde, bi-sulfides and combination thereof.

According to yet another embodiment, each of said first, second and third components is dry, solid or a lyophilate.

According to yet another aspect, the present invention provides a method for preparing a debriding solution, the method comprising:
(a) providing the kit of the invention; and
(b) mixing the components of the kit with at least one diluting solution thereby obtaining a debriding composition having a physiological pH, wherein the proteolytic activity of the said thiol-protease in said debriding solution is within the range of 5,000 to 50,000 USP units/mg.

According to yet another embodiment, the first, second and third components are added in any order with respect to one another, to the at least one diluting solution.

According to yet another embodiment, the debriding solution exhibits debriding activity for at least 6 hours. According to yet another embodiment, the debriding solution exhibits debriding activity for at least 12 hours. According to yet another embodiment, the debriding solution exhibits debriding activity following storage for at least 6 hours at 4-10° C. According to yet another embodiment, the debriding solution exhibits debriding activity following storage for at least 12 hours at 4-10° C.

According to yet another embodiment, the method further comprises:
(c) applying the debriding solution onto the skin lesion or damaged skin; and, optionally,
(d) covering said skin lesion or the damaged skin with a dressing.

According to yet another embodiment, step (d) comprises conveying a flow of the debriding solution through and over said skin lesion or said damaged skin. According to another embodiment, the flow of debriding solution is being conveyed through and over said skin lesion for at least 6 hours. According to yet another embodiment, steps (a) to (d) are iteratively repeated thereby each repeat is carried out with a new portion of the debriding solution.

According to yet another embodiment, the method further comprises storing the debriding solution at ambient temperature or in a temperature within the range of 4-10° C., prior to step (c).

According to yet another embodiment, applying the debriding solution comprises:
applying a flow of the debriding solution onto the skin lesion or the damaged skin and draining said composition therefrom for at least one hour, preferably for at least 6 hours.

According to yet another embodiment, flow is induced by a pump being in fluid communication with at least one reservoir comprising the composition. According to yet another embodiment, flow is induced by and a drip counter.

According to yet another embodiment, the skin lesion is a chronic ulcer. According to yet another embodiment the chronic ulcer is associated with diabetes or prolonged pressure on the wound area.

Other objects, features and advantages of the present invention will become clear from the following description and drawings.

DETAILED DESCRIPTION OF THE INVENTION

Definitions

Figure 1A:
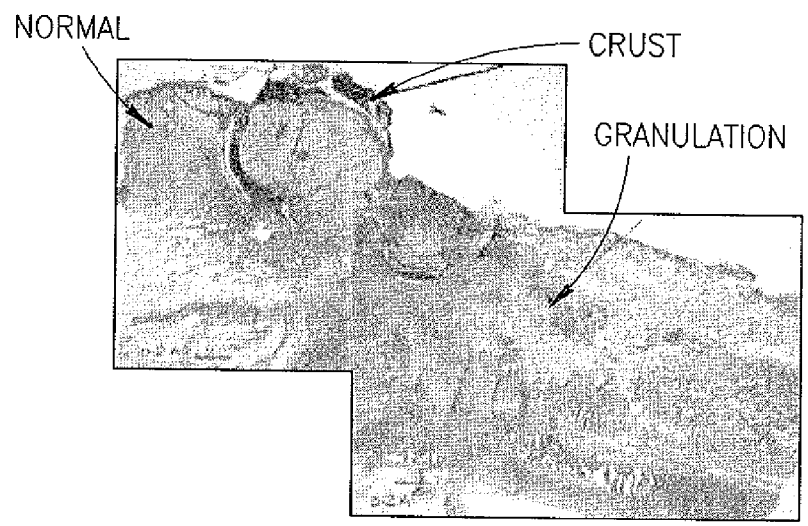
FIG. 1 demonstrates histological sections of porcine wound model treated with a stream of papain solution prepared according to Example 1 for 6 hrs (A) or 11 hrs(B) with respect to control (untreated; C).

The term "papain" as used herein refers to any enzyme of the papain family of thiol proteases derived from plants, which is capable of exerting debriding activity in vitro and in vivo. Papain is a sulfhydryl protease derived from the Carica papaya latex. Native pure papain is partially reactive until activated upon by mild reducing agents such as cysteine, at the free SH functional group thereof. Papain is commercially provided as partially purified crystalline form or crude papain, the later being a mixture comprising papain, chymopapain and lysozyme. According to the principles of the present invention, the term papain refers to papain having an activity within the range of 10,000 to 100,000 US units per mg protein, wherein one USP unit of papain activity is that which releases an equivalent of 1 mg of tyrosine from a casein substrate solution as described in the United States Pharmacopeia reference guide.

The terms "non-active form" or "inactive form" are used herein to describe an enzymatic composition that does not exhibit the intended activity, mainly hydrolysis or proteolysis. Specifically, a non-active form of papain which partially performs or does not perform any substantial hydrolytic or proteolytic activities, which can be stored for months without losing its potential hydrolytic activity.

The term "stable" is used herein to describe non-active enzymatic compositions that retain the desired enzymatic activity upon activation, even after storage in an inactive form. The desired activity of a stable non-active enzymatic composition is readily reestablished, preferably by dilution in suitable solutions, such as solutions comprising at least one thiol compound and at least one buffer that is capable of providing an appropriate pH to the diluted solution. Preferably, a stable non-active enzymatic composition is devoid of particulate material.

The term "reestablished" as used herein refers to restoration of all the well known enzymatic activities of papain, particularly proteolytic activities, i.e. structural breakdown of proteins, in vivo and in vitro.

The terms "hypertonic" and "hyperosmolar" are interchangeably used herein to describe solutions having osmolarity that is at least slightly hypertonic, namely, solutions having a higher osmotic pressure than an isotonic fluid, such as saline. Such solutions include hyperosmolaric saline, and saline comprising at least one osmotic agent being capable of modifying the osmolarity of the solution, particularly, being capable of increasing the osmolarity of an isotonic solution.

The term "ambient temperature" as used herein refers to a temperature within the range of 10 to 30° C., preferably, within the range of 10-25° C.

The term "reversible manner" as used herein refers to the ability of an inhibitor, whether a chemical entity, a biological entity or environmental condition (e.g. pH) to inhibit the activity of an enzyme, particularly a debriding activity of a hydrolytic enzyme, under certain condition which upon canceling such conditions the inhibition effect is annulled. For example, inhibiting the activity of a metalloenzymes by a chelating agent, such as EDTA, may be reversed by the addition of metals in excess. In particular, the term "reversible manner" excludes inhibitors that cause a permanent damage to the enzyme and thereby inhibit the desired enzymatic activity in a non-reversible manner, such as phenylmethansulfonyl fluoride (PMSF).

The term "debridement" as used herein is to be construed in its most general sense and refers to the removal of devitalized tissue from a wound or the removal of dead cells from the surface of the skin, also known as cosmetic peeling.

Preferred Modes for Carrying Out the Invention

While the present invention employs many principles known from the art of proteolytic enzymes and use of same for wound debridement among other therapeutic modalities, the present invention varies from the known art in several critical areas. First, the present invention provides for the first time storable components that can be maintained for weeks and months prior to their intended use as a debriding composition, in ambient conditions, while the potential activity of the components, particularly, enzymatic components, is maintained. Second, obtaining the debriding composition from the storable components is a straightforward procedure, merely including reconstitution in suitable solution(s), which may be carried by any person capable of performing these simple steps and not necessarily by a health-care professional.

Numerous methods for stabilizing enzymatic preparations for the purpose of storage such that the enzymes do not lose their potential activity during storage are known in the art. For example, for metalloenzymes storage in the presence of certain amount of metal chelator(s) such as EDTA, inhibits the enzymatic activity which may be restored by incubating the EDTA-enzyme solution with the metal that is required for the enzymatic activity, typically excess concentrations of such metal/metal ions are required. The metalloenzymes may undergo dialysis before or instead the incubation with the metal chelator such that the metal migrates from the enzymes by osmosis. In such cases, restoration of activity is also achieved by incubating the dialyzed enzyme solution with the metal ion that required restoring the enzymatic activity.

Other methods of storing non-active forms of enzymes include enzyme immobilization in a porous sphere and storage in a buffer containing about 50% glycerol. While each of the aforementioned methods may be potentially suitable for storage of enzymes such that activity can be recovered after storage, in practice, each particular enzyme requires particular storage conditions. If the storage conditions are improper for the enzyme or for the enzymatic activities exerted by same, it would probably remain inactivated. Thus, the present invention is aimed at defining the particular storing conditions for hydrolytic enzymes, particularly cysteine (thiol) proteases such as cysteine proteases derived from plant including papain, bromelain and ficin, particularly papain, although other proteolytic enzymes may possibly be used as long they can be stored and restored according to the principles of the present invention.

The kit of the invention includes at least three separate components for admixture into a debriding composition:
a first component comprising an enzymatic composition comprising a thiol protease in a non-active form, wherein the concentration of the thiol protease in the first component is at least 10-fold higher than the concentration of the thiol protease in the debriding composition;
a second component comprising at least one reducing agent capable of activating the thiol protease, wherein the concentration of the at least one reducing agent is at least 10-fold higher than the concentration of said at least one reducing agent in the debriding composition; and a third component comprising a concentrated buffer solution wherein upon being diluted with the first and second components and at least one diluting solution is capable of maintaining the pH of the resulting debriding composition at a pH within the pH range that is suitable for the activity of the thiol protease, particularly papain, wherein admixing the three components of the kit with at least one diluting solution provides a debriding composition having a physiological pH and further having a proteolytic activity within the range of 10,000 to 100,000 USP units/mg.

Alternatively, the kit comprises at least one diluting solution instead of the third component, said at least one diluting solution comprises at least one buffering agent, at least one chelating agent, wherein said at least one dilution solution being isotonic or hypertonic.

Preferably, the reducing agent of the kit is stored in a container consisting of glass or quartz and more preferably in a nitrogen atmosphere or under vacuum.

According to the principles of the present invention, the thiol protease contained within the kit of the invention is preferably having an activity of at least 30,000 USP units per 1 mg. At such activity, the concentration of the thiol protease in the concentrated solution and also in the final solution may be lowered thereby enabling lowering the volume of the concentrated solutions of the kit.

According to one embodiment, the volume ratio between each component of the kit and the volume of the debriding composition is at least 1:10. According to another embodiment, said volume ratio is at least 1:20. The final solution may be of about 500 ml, and accordingly may be kept in an infusion bag. Thus, the volume of each one of the components of the kit is at most 50 ml per component, preferably at most 25 ml per component, more preferably at most 12.5 ml per component.

The components of the kit are stable upon storage for weeks and months in room temperature, or in a temperature within the range of 4-10° C., prior to being admixed with one another and with the at least one diluting solution to provide an enzymatic composition having a debriding activity.

Although, the components of the kit of the invention are preferably maintained and stored in the form of concentrated solutions, the components may be maintained in a dry or solid form (e.g. lyophilized), optionally under vacuum. Restoration of a dry composition requires dissolution under particular gentle conditions as improper dissolution, namely, dissolution under heat or vigorous shaking, may result in complete or partial protein inactivation. Incomplete dissolution may further result in improper concentrations of the components within the final debriding composition, thereby lower or lack of debriding activity.

Storage means appropriate for storing each one of the components of the kit in a single container or in separate containers, may be any container made of inert materials that do not interact with the content of each component and that are stable under the storage conditions. Thus, suitable containers for storing each components of the kit include a bag, a bottle, a vial, a large volume parenteral, a small volume parenteral, a prefilled syringe or a cassette. Storage conditions include sterile or aseptic conditions, i.e. each component is preferably maintained sterile or aseptic. Alternatively, the content of each container may be readily sterilized. Furthermore, in preferred embodiment, the whole or partial content of each container may be withdrawn while maintaining the container uncontaminated.

In order to maintain the highly concentrated enzyme solution of the first component inactive and stable for weeks and months, and particularly, in order to avoid self digestion, precipitation, aggregation and irreversible inactivation during storage, the inventors of the present invention have found that the solution should be maintained at acidic pH, particularly at a pH within the range of 3 to 6, preferably 4 to 5. Under such conditions, the potential activity of the thiol protease is maintained while the thiol protease does not precipitate, disintegrate, being self digested or aggregate. In addition, the buffer acetate that remains in the final debriding composition, after the first component of the kit is admixed with the other components and the at least one diluting solution, does not interfere substantially with the debriding activity of the thiol protease. The fact that the thiol protease under such storage conditions does not form aggregates and/or precipitate is particularly unexpected in view of the fact that in the solution of the first component, the concentration of the thiol protease is extremely high and is at least 20 mg/ml, up to about 100 mg/ml.

Buffers having a buffer capacity at a pH range of 3-6 are preferred. Such buffers include, but are not limited to, succinate buffer, maleate buffer, citrate buffer, MES buffer, acetate buffer and combinations thereof.

The second component comprises a reducing substance containing a thiol moiety, wherein the reducing substance is capable of activating thiol-proteins. The concentration of the reducing substance within the second component is substantially high, particularly, at least 10-fold higher than its concentration in the final debriding composition. Although highly concentrated, the reducing agent does not precipitate, aggregate or lose its potential activity during storage. Suitable reducing agents include, but are not limited to, sulfide, cysteine and cysteine hydrochloride.

The kit further comprises a third component comprising a concentrated buffer solution such that when the third component is admixed with said second component, said first component and the at least one diluting solution (also termed hereinafter "carrier"), the buffer solution is diluted thus capable of maintaining the debriding composition in a pH range which enables the debriding activity of the thiol protease and at the same time suitable for physiological application, i.e. the intended use of the debriding composition. Thus although the pH range that is optimal for thiol proteases, particularly papain is relatively wide, the debriding composition of the invention is within a physiologically acceptable pH range, namely, within the range of 6.8 to 7.7, preferably within the range of 7 to 7.6. The concentration of the buffer in the third component is high, particularly at least 10-fold higher than the concentration of the buffer in the final debriding solution.

The third component further comprises at least one chelating agent.

The at least one diluting solution being admixed with all the components of the kit of the invention to form the debriding composition may be provided in a separate container with a measuring mean which enables measuring the exact volume of carrier required to be admixed with the components of the kit. Alternatively, the carrier may be a component of the kit at the exact volume required to be admixed with the other components in order to form the debriding composition. The carrier may be provided in a container to which each one of the components of the kit of the invention is added to form the final debriding composition in the container. The container may be a bag, a bottle, a vial, a large volume parenteral, a small volume parenteral, a prefilled syringe or a cassette. The order to addition of each component to the at least one diluting solution is insignificant. Preferably, the at least one diluting solution is aseptic or sterile or may be readily treated for the purpose of becoming aseptic or sterile. Moreover, during mixing of the components of the kit with the at least one diluting solution the mixture is preferably maintained uncontaminated. According to certain embodiment, mixing is typically performed under aseptic/sterile condition.

The carrier may be a hyperosmolaric solution such as hyperosmolaric saline solution, saline solution comprising osmotic agent(s) and hyperosmolaric saline solution comprising osmotic agent(s).

High osmolarity is a known treatment means of infections, as it prevents the growth of bacteria. The present invention discloses for the first time that using such hyperosmolar solution, encourages ulcer and wound healing by inducing or enhancing hyperemia.

The kits, compositions and methods of the present invention are directed for providing an advantageous treatment for wounds, particularly ulcers, and preferably chronic ulcer such as diabetic ulcers. About 16 million people in the United States have diabetes and approximately 15 percent develop chronic ulcers of the foot and leg that are slow-healing open wounds. Patients with diabetic ulcers are at higher risk for local and systemic infections and amputation. A majority of diabetic ulcers are quite deep and also have an inadequate blood supply.

Because the pain of small cuts or scrapes may not be felt due to nerve damage in the area, and on top of that, poor circulation slows healing time, such ulcer may develop into dangerous wounds before diagnosed. Pressure ulcers also known as bedsores or decubitus ulcers may also develop into severe ulcers that may be lethal. In the event of pressure ulcers, the ulcerated area of skin and tissue becomes injured or broken down typically as a consequence of an extended period of uninterrupted pressure or other continuing assault to the skin. Typically, pressure sores develop when the skin and underlying tissue is squeezed between a bone and an external surface, such as a bed or chair. The most common places for pressure ulcers are over bony prominences, such as the elbow, heels, hips, tailbone, ankles, shoulders, back, and the back of the head. Generally, pressure ulcers occur when a person is in a sitting or lying position for too long without shifting his or her weight. Thus, while anyone confined to a chair or bed is at risk, it is more commonly observed in the elderly and infirm. Incontinence and decreased sensory perception, e.g., due to a stroke, also increase the likelihood of developing bedsores. The constant pressure against the skin squeezes the blood vessels that supply nutrients and oxygen to the skin and nearby tissue partially or completely closed, causing a decreased blood supply to the area. The absence or severe reduction of oxygen and nutrients, results in the death of the skin and, potentially, underlying tissues. Left untreated, nearby tissue begins to die, eventually resulting in an ulcer that can also affect the bone. Severe ulceration, i.e., resulting in an opening in the skin can provide an entry for secondary infections; in particularly severe cases decubitus ulcers can result in death.

Treatment and Dosing Regimens

The typical dose useful for debriding necrotic tissue according to the present invention is determined according to the severity of the lesion. Commonly, a flow of a debriding solution comprising a thiol protease according to any one of the formulations detailed herein, is conveyed over and through the lesion for at least one hour. The lesion is monitored for assessing the progress of debridement. A pause in the treatment for short time periods is carried out by arrest of the flow and removal of any conduits that prevent a free movement of the patient. An occlusive dressing to which the conduits are reattached may be left over the lesion.

Treatment may be applied using an apparatus as described in US2004/0186421 or WO2005/070480 of the inventor of the present invention. Such apparatus comprise a housing having at least one aperture formed therein and means for affixing the apparatus to the skin around the circumference of the skin lesion, wherein said housing comprises (i) at least one inlet tube having a first longitudinal axis and configured to be adjustable along its longitudinal axis through said at least one aperture; and (ii) at least one outlet tube having a second longitudinal axis. The apparatus further comprises a reservoir adapted for holding the debriding solution, the reservoir being in fluid communication with the one or more inlets. An outlet may comprise valves for controlling the flow between the reservoir and the treatment zone. Preferably, an outlet may further comprise means enabling disconnecting and reconnecting the housing from the reservoir, thereby enabling to pause the treatment.

The simplicity of disconnecting and reconnecting the patient from the flow means and the debriding compositions enables applying the debriding treatment prolonged periods. A flow of the debriding solution may last for at least one hour and may also last for several hours, depending on individual needs.

EXAMPLES

Example 1

Preparation of a Debriding Composition I from Stable and Clear Concentrated Solutions A kit containing the following components was provided:
1. An enzymatic solution (25 ml) of papain (Merck Cat. No. 1.07149.5000 with specific activity of 30,000 USP U/mg, 40 mg/ml) in 0.05 M acetate buffer, pH 4.3-4.5 containing 10% (v/v) glycerol.
2. Cysteine hydrochloride, 25 ml, 0.1 M, pH 1.4.
3. Tris/EDTA, 25 ml of 2M/0.04 M, pH 7.85

All solutions were clear and did not contain precipitates or aggregates. The three solutions were diluted by their addition into 500 ml solution containing 0.9% saline to provide a solution having a final pH of 7.4±0.2 and final concentrations of Tris buffer 0.1M, cysteine HCl 5 mM, EDTA 2 mM, 2 mg/ml papain and 0.5% glycerol in 0.9% saline.

Example 2

Preparation of a Debriding Composition II from Stable and Clear Concentrated Solutions A kit containing the following components was provided:
1. An enzymatic solution (25 ml) of papain (Merck Cat. No. 1.07149.5000 with specific activity of 30,000 USP U/mg, 40 mg/ml) in 0.05 M acetate buffer, pH 4.3-4.5 containing 10%(V/V) glycerol.
2. Cysteine hydrochloride, 25 ml, 0.1 M, pH 1.4.
3. Tris/EDTA, 25 ml of 2M/0.04 M, pH 7.85

All solutions were clear and did not contain precipitates or aggregates. The three solutions were diluted by their addition into 500 ml solution containing 5% (W/V) saline to provide a hyperosmolaric solution having a final pH of 7.4±0.2 and final concentrations of Tris buffer 0.1M, cysteine HCl 5 mM, EDTA 2 mM, 2 mg/ml papain and 0.5% glycerol in 5% saline.

Example 3

Preparation of a Debriding Composition III from Stable and Clear Concentrated Solutions A kit containing the following components was provided:
1. An enzymatic solution (25 ml) of papain (Merck Cat. No. 1.07149.5000 with specific activity of 30,000 USP U/mg, 40 mg/ml) in 0.05 M acetate buffer, pH 4.3-4.5 containing 10%(v/v) glycerol.
2. Cysteine hydrochloride, 25 ml, 0.1 M, pH 1.4.
3. Tris/EDTA, 25 ml of 2M/0.04 M, pH 7.85

All solutions were clear and did not contain precipitates or aggregates. The three solutions were diluted by their addition into 500 ml solution containing 10% (v/v) glycerol to provide a hyperosmolaric solution having a final pH of 7.4±0.2 and final concentrations of Tris buffer 0.1M, cysteine HCl 5 mM, EDTA 2 mM, 2 mg/ml papain in 10.5% glycerol.

Example 4

Preparation of a Debriding Composition IV from Stable and Clear Concentrated Solutions A kit containing the following components was provided:
1. An enzymatic solution (25 ml) of papain (Merck Cat. No. 1.07149.5000 with specific activity of 30,000 USP U/mg, 40 mg/ml) in 0.05 M acetate buffer, pH 4.3-4.5 containing 10%(V/V) glycerol.
2. Cysteine hydrochloride, 25 ml, 0.1 M, pH 1.4.
3. Tris/EDTA, 25 ml of 2M/0.04 M, pH 7.85

All solutions were clear and did not contain precipitates or aggregates. The three solutions were diluted by their addition into 500 ml solution containing 10% (v/v) glycerol and 0.9% (W/V) saline to provide a hyperosmolaric solution having a final pH of 7.4±0.2 and final concentrations of Tris buffer 0.1M, cysteine HCl 5 mM, EDTA 2 mM, 2 mg/ml papain in 10.5% glycerol in 0.9% saline.

Example 5

Preparation of a Debriding Composition V from Stable and Clear Concentrated Solutions A kit containing the following components was provided:
1. An enzymatic solution (25 ml) of papain (Merck Cat. No. 1.07149.5000 with specific activity of 30,000 USP U/mg, 40 mg/ml) in 0.05 M acetate buffer, pH 4.3-4.5 containing 10%(V/V) glycerol.
2. Cysteine hydrochloride, 25 ml, 0.1 M, pH 1.4.
3. Tris/EDTA, 25 ml of 2M/0.04 M, pH 7.85

All solutions were clear and did not contain precipitates or aggregates. The three solutions were diluted by their addition into 500 ml solution containing 10% (v/v) glycerol and 5% (w/v) saline to provide a hyperosmolaric solution having a final pH of 7.4±0.2 and final concentrations of Tris buffer 0.1M, cysteine HCl 5 mM, EDTA 2 mM, 2 mg/ml papain in 10.5% glycerol in 5% saline.

Example 6

Wound Debridement by Streaming a Debriding Solution Onto a Porcine Wound Model I Animal Preparation and Treatment Protocol:
Mature Large white female porcine, weighing approximately 30 kg was sedated and anesthetized with intramuscular injection of Ketamin (100 mg/ml) 20 mg/kg BW, Xylasine 10% (2 mg/kg BW) and Atropine 0.02 mg/kg BW. Pig was maintained under general anesthesia on an inhaled mixture of halothane and isoflurane (1.5-3%) in pure oxygen and by intravenously infusion of Hartman Solution (Ringer Lactate) at constant rate of 30-50 drops/min Five skin myocutaneous double flap wounds were induced on the dorsal plane of the pigs' backs, in the para-vertebral regions, 9×3 cm in size, (extending into the muscular layer) according to Swindle (Swindle MM. Surgery, anesthesia and experimental techniques in swine. Iowa State University Press, USA. pp 74-77. 1998). Seven days post wound induction, under general anesthesia, the wounds were exposed providing 3.5 cm×3.5 cm opening and devices (Dermastream™; WO03/011369, US 2004/0186421 and WO2005/070480) were placed over the wound and attached to skin surroundings and their inlet and outlet parts were connected to solution reservoir and fluid collecting bags, respectively.

Four out of 5 wounds were subjected to 6-11 hrs controlled streaming of enzyme or saline solution for a period of 6-11 hours at a flow rate of 1 ml/min. One wound served as control non-treated.

The debriding enzyme solution contained Papain (Merck Cat. No 1.07149.5000, with specific activity of 30,000 USP U/mg) at a concentration of 60,000 USP-U/ml, prepared according to Example 1.

Following the 6-11 hrs treatment, streaming was terminated, DermaStream™ was removed from all wounds and photographic documentation of the surface of each wound area was performed by S3 Pro zoom Nikon camera at distance of 20 cm from wound surface and angle of ~45° w at high resolution. The area included the entire wound site and margins.

Pigs were sacrificed by intramuscular injection of Pental (200 mg/ml) 1 ml/1.5 kg BW and biopsies were excised from all wounds, containing lengthwise sampling of wound area, 1×4 cm in size. The biopsies included normal skin margin as well as underlying non wounded muscle layers. The samples were fixed in 4% paraformaldehyde for 48 hrs and embedded in paraffin. One random and representative section/slice (8 μm), running from normal margin to edge of wound margin, was collected from each block and stained with Hematoxylin Eosin stain technique.

Figure 1B:
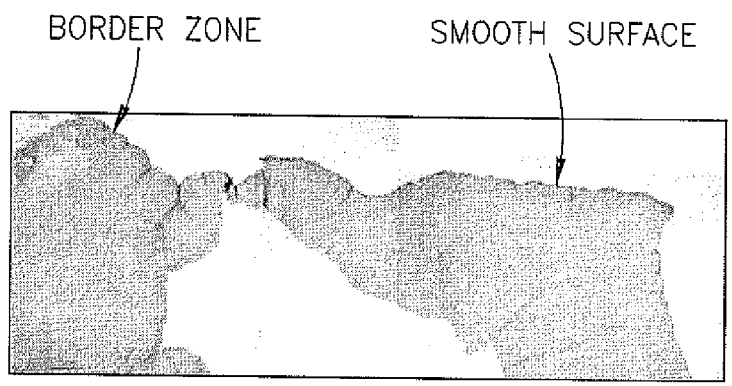
Figure 1C:
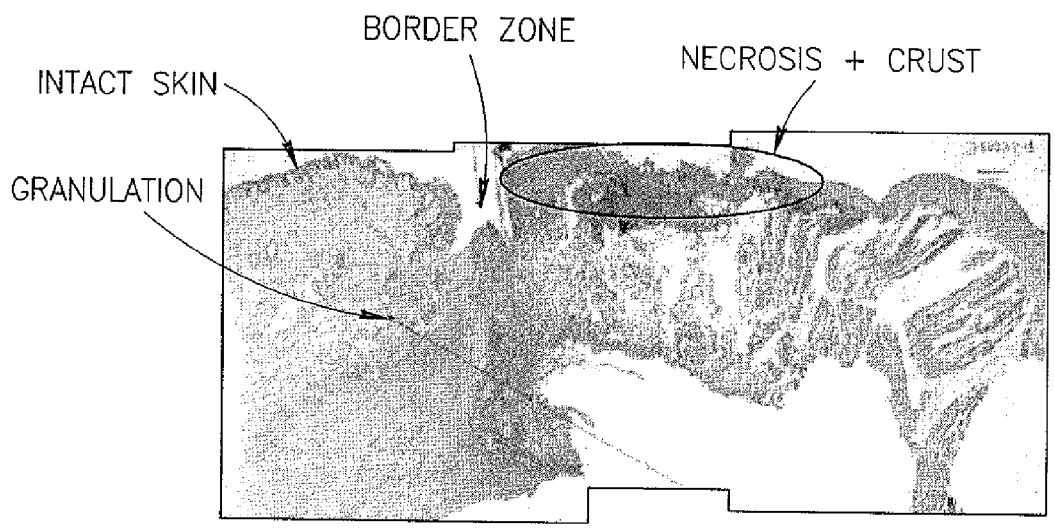

The debriding effect of streaming papain solution prepared according to Example 1 for 6 hrs or 11 hrs on a porcine wound model is presented in histological sections shown in FIG. 1, comparing to an untreated wound. The results clearly indicate a significant debridement affected already after single treatment of 6 hrs.

Example 7

Figure 2A:
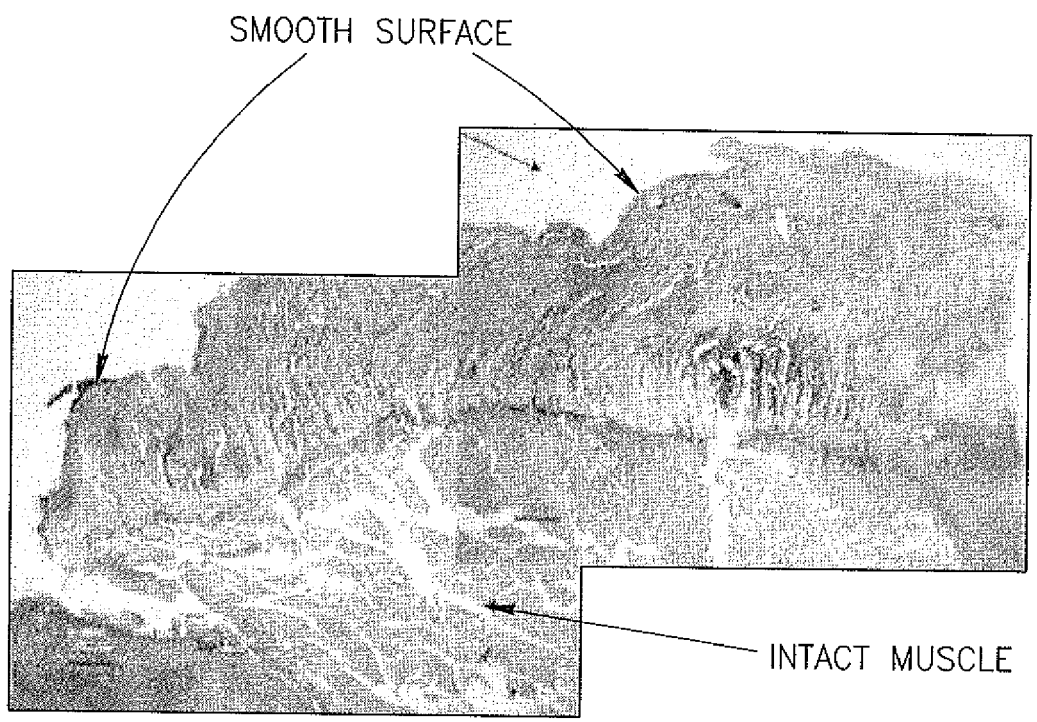
FIG. 2 exhibits histological sections of porcine wound model treated with a stream of papain solution prepared according to Example 2 for 6 hrs (A) or 11 hrs(B).
Figure 2B:
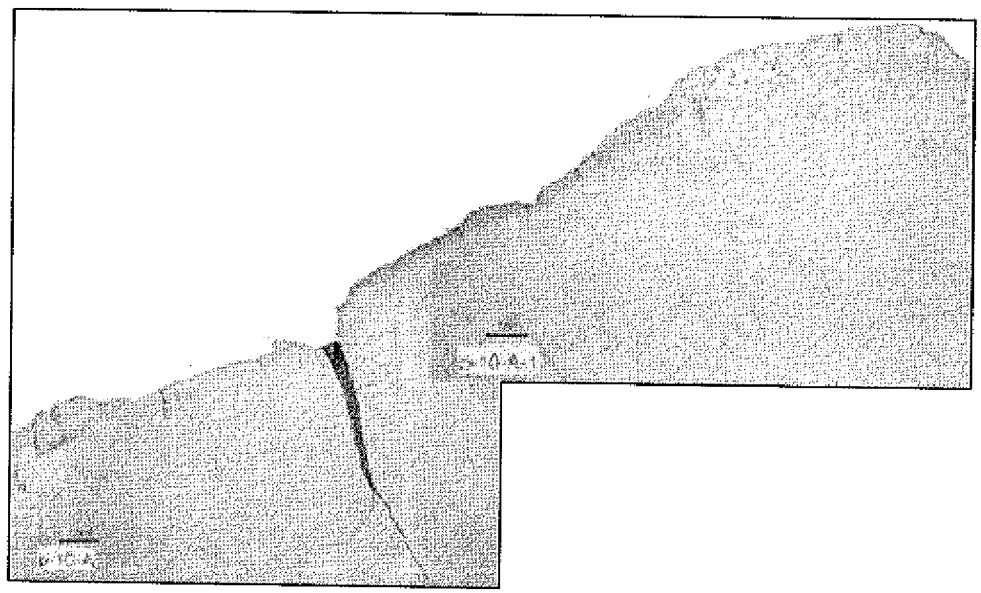

Wound Debridement by Streaming a Debriding Solution Onto a Porcine Wound Model II Results of streaming of the solution described in Example 2 was applied onto a different porcine wound for 6 hrs or 11 hrs, employing the experimental setup described in Example 6 are presented in FIG. 2. The results indicate effective debridement achieved already after 6 hrs and a substantial cleanup attained within 11 hrs with distinctive appearance of hyperemia.

Example 8

Figure 3A:
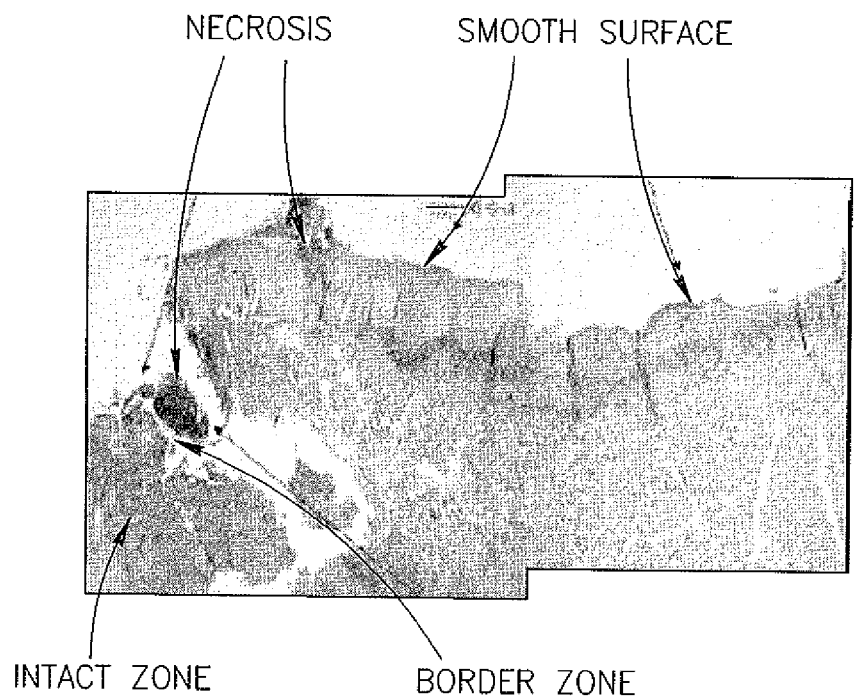
FIG. 3 presents histological sections of porcine wound model treated with a stream of papain solution prepared according to Example 3 for 6 hrs (A) or 11 hrs (B).
Figure 3B:
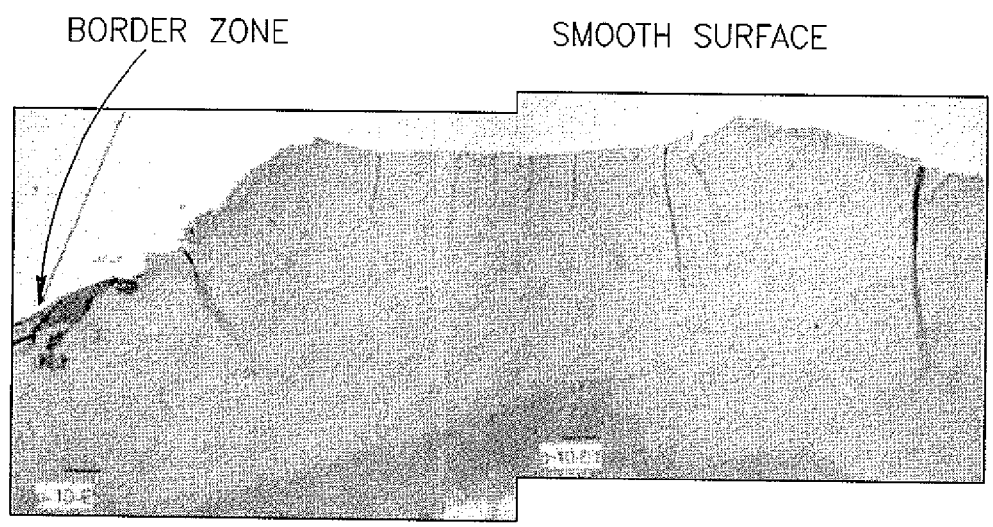

Wound Debridement by Streaming of Solution Prepared According to the Invention Onto a Porcine Wound Model III Results of streaming of the solution described in Example 3 for 6 hrs and 11 hrs employing the experimental setup described in Example 6 are presented in FIG. 3. Results indicate effective debridement achieved already after 6 hrs.

Example 9

Figure 4:
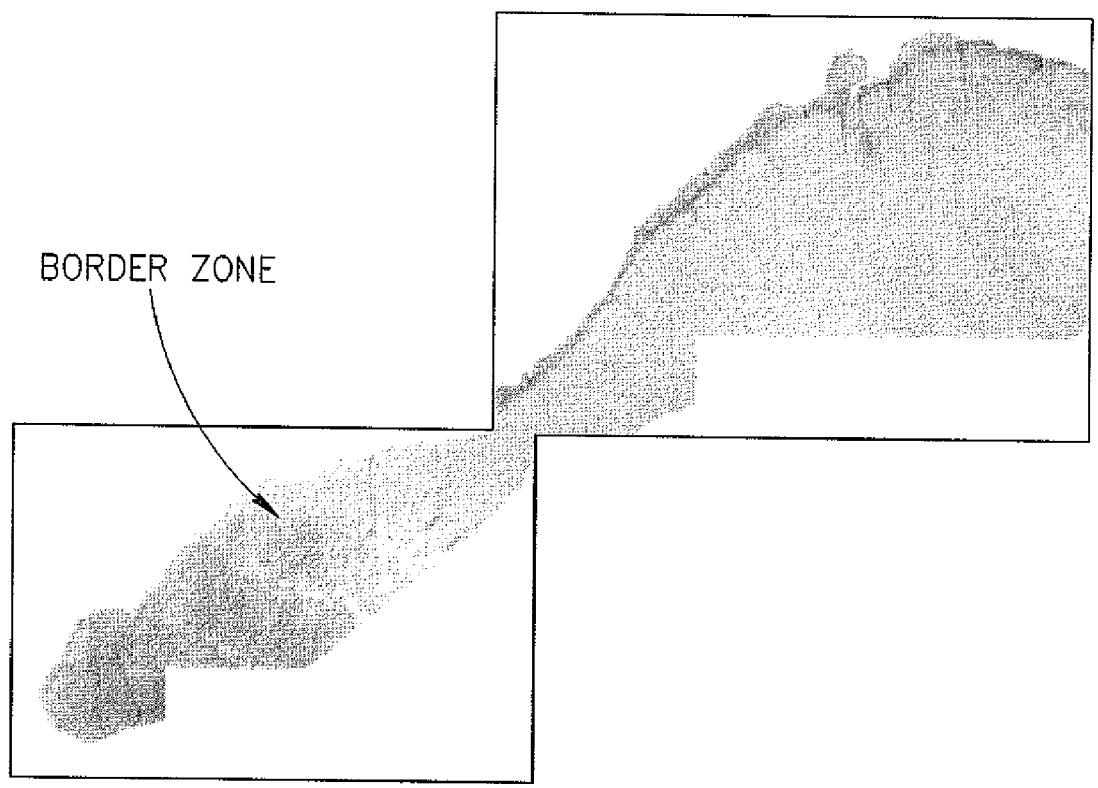
FIG. 4 shows histological sections of porcine wound model treated with a stream of papain solution prepared according to Example 5 for 11 hrs.

Wound Debridement by Streaming of Solution Prepared According to the Invention Onto a Porcine Wound Model IV Results of streaming of the solution described in Example 5 for 11 hrs employing the experimental setup described in Example 6 are presented in FIG. 4. Results indicate effective debridement.

Figure 5A:
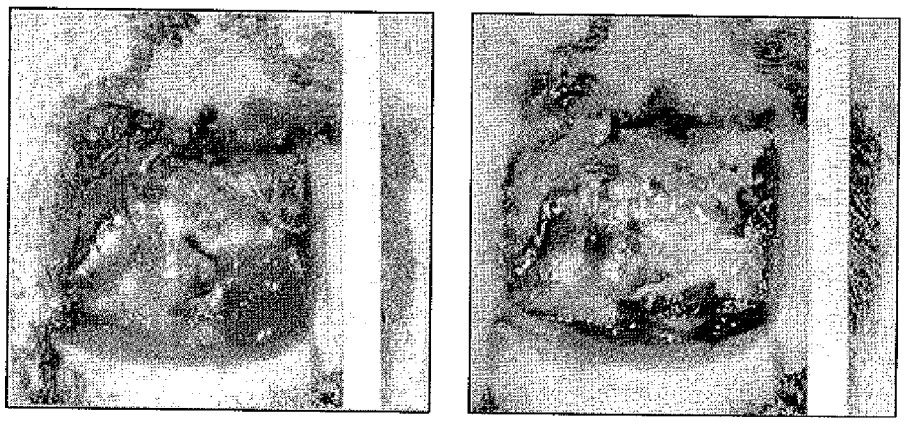
FIG. 5 demonstrates the impact of different debriding solutions on the morphology and appearance of necrotic wound debridement.
Figure 5B:
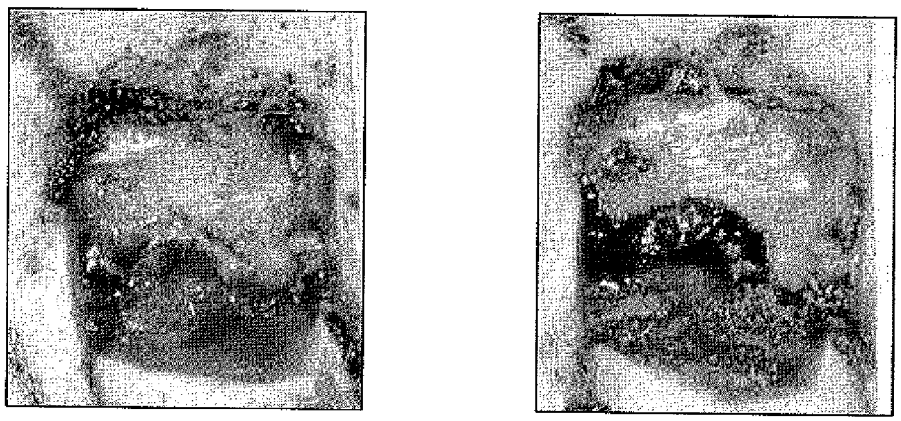
Figure 5C:
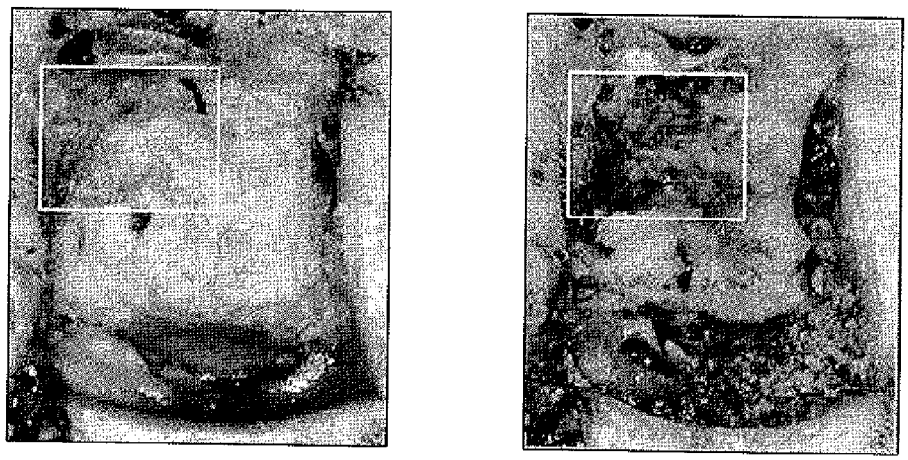

The impact of different debriding compositions on the morphology and appearance of necrotic wound debridement is demonstrated in FIG. 5: A—papain (40 mg/ml) in saline 5% for 6 hr (left panels—before treatment and right panels—after treatment); B—papain (40 mg/ml) in saline 0.9% and glycerol 10% for 6 hr; C—papain (40 mg/ml) in saline 5% and glycerol 10% for 6 hr.

Example 10

Safety Test—Acute Skin Irritation

Acute Skin Irritation study was conducted in female New Zealand (NZW) rabbits (n=3), 3.0-3.4 kg for the assessment of the potential of dermal irritation reaction of a debriding solution comprising 2 mg/ml (also termed hereinafter "Enzystream™").

In all rabbits, 4-24 hrs before the application of the tested solutions onto designated sites on rabbit's backs, the fur was removed by closely clipping both sides of the spine. On each rabbit's back, 2 control sites and 2 treated sites, approximately 2.5×2.5 cm each, were prepared. The two tested sites on each rabbit were subjected to 0.5 ml of Enzystream™ final debriding solution and the remaining 2 tested sites were treated with same volume of saline. The tested solutions were first applied to gauze patches which were then applied directly to the respective sites for a period of 4 hrs. At the end of the 4 hrs exposure period, the patches were removed.

Observation and Examination: Rabbits were observed for a period of 72 hrs following removal of the patches. Extended observation period beyond 72 hrs was done in cases of persistent skin reactions and animal was observed once daily until reversibility was seen or up to a maximum of 14 days post application. Signs of erythema and edema (according to grades of skin reactions) and response at the application sites were evaluated after 1, 4, 24, 48 and 72 hrs post treatment. In cases where the animals were monitored for up to 14 days, further examinations were performed once daily. Examination of any systemic adverse effects were carried out once daily throughout the study period.

Body weights were measured before the solution application to test sites and at study termination (after 72 hrs or 14 days in case of extended observation period).

Data evaluation: The evaluation of the tested solutions potential irritation effects was based on the determination of the Primary Irritation Index (PII) scale using the Draize irritation index for erythema & edema (Draize, UL.: Dermal toxicity in appraisal of the safety of chemicals in food, drugs and cosmetics. The association of food and drug officials of the United States, Bureau of food and drug, Austin, Tex. 1959 Pages: 46-59) and was compared to the "irritation response categories in the rabbit" as specified in ISO 10993-10. The PII of the application sites was evaluated: immediately at 1 hr, after 4 hrs patch application and at 24, 48 and 72 hrs post treatment.

Results: The overall dermal irritation responses in all rabbits resulted in "negligible" to "slight" reaction according to the PII score (0-1.9) with an average of 1.05 ("slight"). Furthermore, no clinical signs in response to any tested solution were evident in any of the rabbits as well as no abnormal changes in body weight throughout of the entire studies periods.

Example 11

Safety Test—Acute Toxicology During 1 Hour Infusion

Acute toxicology study of 1 hr i.v. infusion of EnzyStream™ solution in male Sprague Dawley rats (n=12), 270-275 gr, for safety assessment.

All rats were anesthetized with halothane gas anesthesia during 70-80 min for jugular via catheter insertion and infusion. A polyethylene catheter filled with saline-heparin was inserted into the jugular vein. Slow automatic infusion of tested formulations (control-saline or Enzystream™ solution) was performed of 1 ml of a 1 mg/ml papain solution throughout one hour. Five rats were subjected to saline while 7 rats were treated with EnzyStream™ solution.

Dosage rationale: The amount of solution administered was 1 ml/animal weighing ~250 g. The concentration of the administered papain enzyme was 1mg/ml. These amounts were calculated according to animal and human body weights and blood circulation volumes to represent potential absorption of 50% of streamed enzyme solution by a treated wound area during one session of streaming in clinical trials. It may be assumed that this value is ~×100 higher than the amount that may be practically absorbed during treatment of venous/diabetic ulcers in clinical trials. This assumption is based on the poor blood circulation of diabetic and venous ulcers and it may be assumed that fluid penetration into body/blood system is hence minimal One hour post infusion, the catheter was withdrawn and vein and skin were sutured Animals were monitored for the following 14 days and sacrificed by injection of Pental (200 mg/ml) 1 ml/1.5 kg BW.

Physiological and biochemical parameters: Body weight (BW) was measured before i.v. infusion and at 24, 48, 72 hrs, 7 and 14 days post infusion.

Temperature and Electrocardiograms (ECG) were measured before infusion, every 10 min throughout the infusion and at 3, 24, 48, 72 hrs, 7 and 14 days post infusion.

Blood samples were obtained from tail vein for CBC, liver and kidney functions, and electrolytes prior to infusion period and at 3, 24, 48, 72 hrs, 7 and 14 days post infusion.

Vitality and normal behavior patterns of eating, drinking, urinary and fecal secretions were monitored daily.

Histology: After 14 days, biopsies from the following main organs: heart; lung; kidney & adrenal; liver; esophagus; trachea; thyroid; pancreas; thymus; xyphoid cartilage; spleen and knee joint were removed from all rats and immediately fixed in four-percent phosphate buffered formaldehyde for 48 hours, processed by routine histological procedures and embedded in paraffin.

Serial sections were cut at 8 μm thickness. The sections were stained with hematoxylin and eosin and were taken for histological examination for toxic effects.

Results: During acclimation period prior to initiation of i.v. infusion, all monitored parameters of the rats were within the normal physiological ranges. Body Weight (BW), rectal Temperature, heart rate, blood tests for liver and renal functions as well as for blood electrolytes levels—showed no statistical differences between the saline control and the experimental treated groups and were all within the normal data range. Similar dynamic profile of BW changes was demonstrated in experimental and control groups: BW decreased slightly during the first 3 days post infusion procedure and began to increase at day 4 and finally was even higher than the pre-infusion BW data.

No abnormalities were detected in the histological sections of 12 examined inner organs from both animal groups. At histological level, all organs and tissues of all animals tested (saline-treated or papain-treated), showed normal histological pattern without pathological, morphological changes or other adverse effects The results obtained under the experimental conditions described above clearly demonstrate absence of any toxic side effects for Enzystream™ debriding solution tested formulation infused for 1 hr in rats.

Example 12

Safety Test—Acute Toxicology During 6 Hour Infusion

Safety evaluation of intravenous infusion of Enzystream™ solution at the same dose described in Example 11 (one ml of 1 mg/ml papain solution) throughout prolonged acute intravenous (i.v.) infusion of 6 hrs was conducted in 8 Sprague Dawley rats (4 males and 4 females), 270-275 gr, anaesthetized conscious rats.

Figure 6:
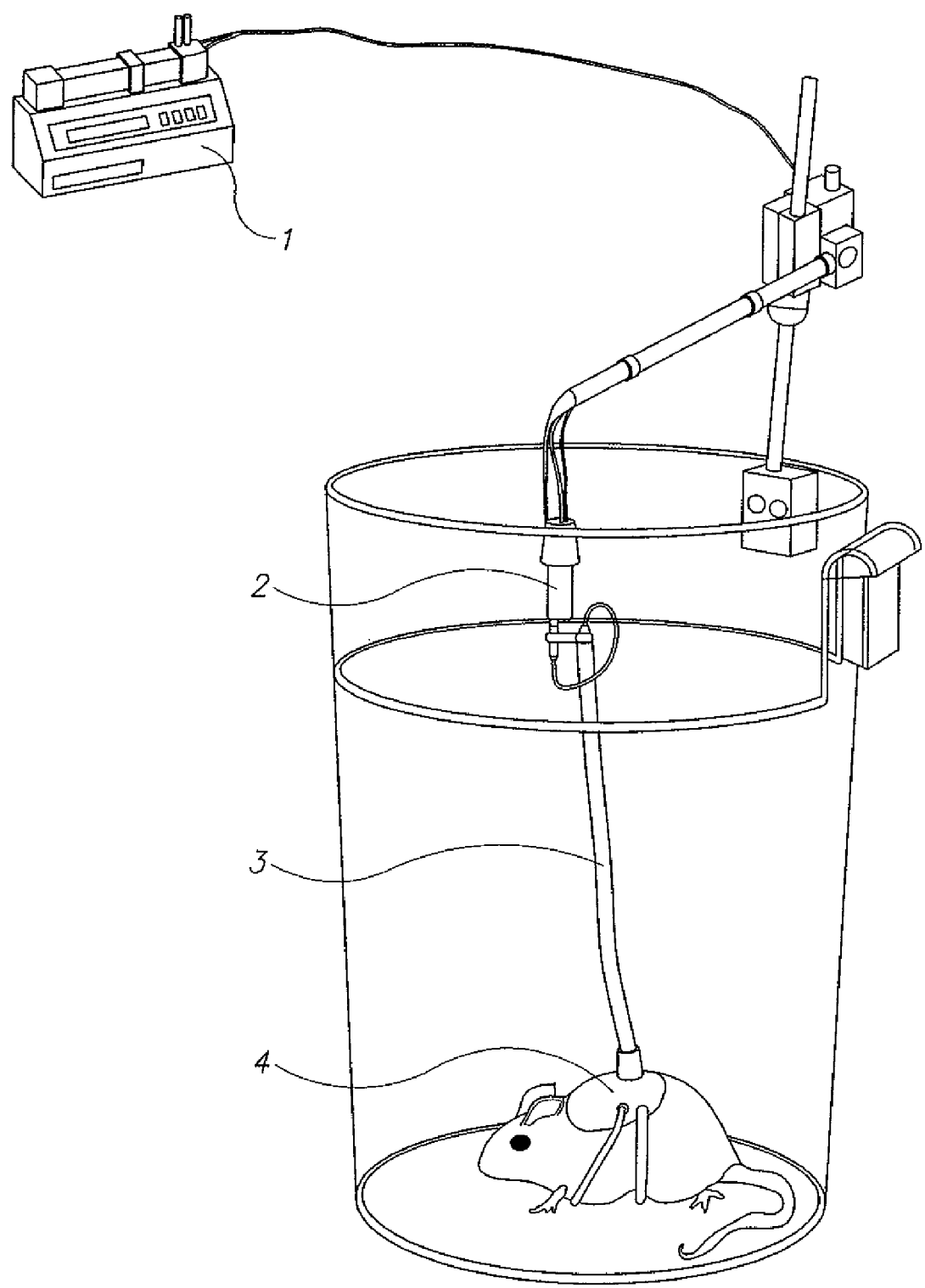
FIG. 6 depicts an infusion pump system for i.v. infusion in rodents.

Methods: All rats were analgesized with a single subcutaneous injection of Flunixin Meglumin and thereafter anesthetized by injection of Ketamine-Xylasine for the experimental setup preparation. A polyethylene tube filled with heparinized saline solution was inserted into the jugular vein. After about an hour when animals return to a state of consciousness, initiation of slow automatic infusion of tested formulations (control-saline or Enzystream™) was performed by infusion pump 1 connected to one end of an elongated passageway 3 through a swivel 2, wherein the second end of the passageway 3 is in communication with the animal's skin through the tether and saddle 4 (FIG. 6). Passageway 3 may comprise a stainless steel spring. The rate of infusion was 2.77 µl/min of one ml of the 1 mg/ml papain solution during 6 hrs. Four rats were subjected to saline infusion while 4 other rats were administered by Enzystream™ solution.

Following 6 hrs of infusion, the cannula was withdrawn and vein and skin were sutured. Animals were monitored for 14 days and euthanized by $CO_2$ asphyxiation.

Physiological and biochemical parameters: Body weight was measured before i.v. infusion and at 2, 4, 7 and 14 days post infusion.

Clinical signs were recorded daily throughout the entire 14-day observation period. Observations included changes in skin, fur, eyes, mucous membranes, occurrence of secretions and excretions, autonomic activity (e.g. lacrimation, salivation, piloerection, pupil size, and unusual respiratory pattern).

Vitality and normal behavior patterns of eating, drinking, urinary and fecal secretions were also monitored daily.

Blood samples for CBC, liver and kidney functions, and electrolytes were obtained from jugular vein by the cannula prior to infusion period and after 24 hrs. At termination of the observation period, prior to sacrifice, blood sample was obtained from the retro-orbital sinus.

Histology: Biopsies from the following main organs: heart; lung; kidney & adrenal; liver; esophagus; trachea; thyroid; pancreas; thymus; xyphoid cartilage; spleen, knee joint and brain were removed from all rats and immediately preserved in 4% formaldehyde solution for 48 hours, processed by routine histological procedures and embedded in paraffin. Serial sections were cut at 8 µm thickness. The sections were stained with hematoxylin and eosin and were taken for histological examination for toxic effects.

Results: During acclimation period prior to initiation of i.v. infusion, all monitored parameters of the rats were within the normal physiological range.

Physiological parameters: No noticeable clinical signs were evident throughout the entire study period in the control saline-treated or the Enzystream™ treated rats.

Body weight determinations revealed in both groups a slight and transient BW loss on day 2 and 4 but on day 7 post infusion, all animals in both groups demonstrated weight gain.

Examination of clinical chemistry parameters such as liver and renal functions and electrolytes in blood samples collected before and subsequently 24 hrs post infusion were within normal range in both control and Enzystream™ treated groups. Determination of both hematology and biochemistry parameters obtained at termination of 14-day study period from both groups revealed values that were all within normal range as well.

Histological findings: At necropsy level, no gross pathological findings were observed in both groups. At the histological level, all organs and tissues of all animals (saline-treated or Enzystream™-treated), showed normal histological pattern without any pathological, morphological changes or other adverse effects.

Conclusions: The results obtained in this safety study under the experimental conditions described above, clearly demonstrate that there are no toxic side effects for Enzystream™ debriding solution when infused intravenously for 6 hrs.

Example 13

Shelf Life

Storage (shelf life) stability of concentrated papain solution containing variable amounts of glycerol and NaCl and stored at 4° C.

Methods: Three concentrated enzyme solutions were prepared (40 mg/ml papain 30,000 USP-U/mg each), containing variable amounts of glycerol and NaCl as follows: (I) 5% Glycerol+0% NaCl; (II) 30% Glycerol+0% NaCl and (III) 30% Glycerol+18% NaCl. The concentrated enzyme solutions were stored at 4° C., in tightly sealed tubes wrapped in aluminum foil until use.

At each check point a sample was removed from each tube and subjected to a standard BAPNA substrate papain bioassay preformed with freshly prepared buffer and cysteine activator solutions.

The residual enzymatic activity was characterized by comparing reaction's slope for 10 min at 410 nm.

Figure 7A:
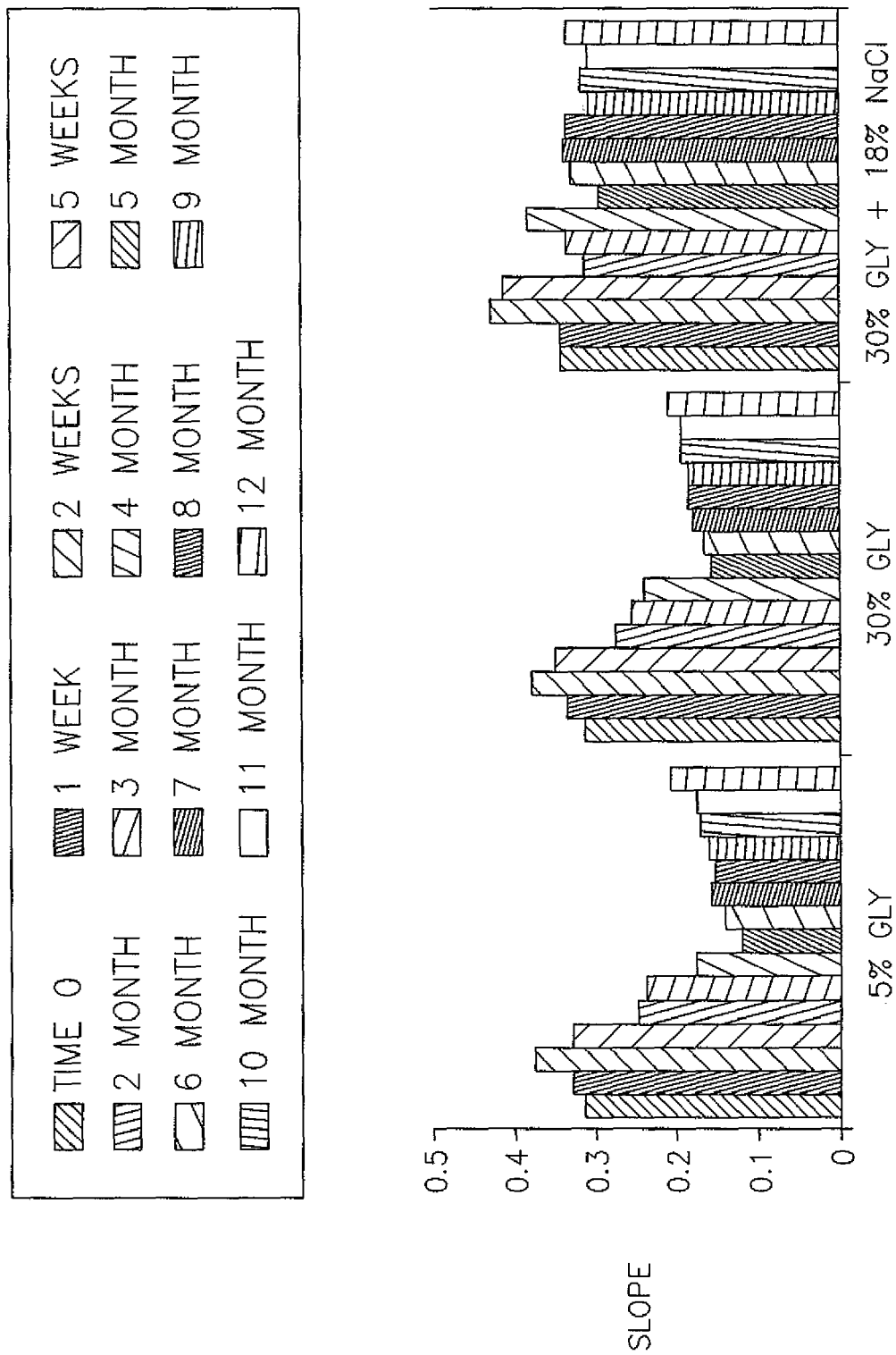
FIGS. 7A and 7B present the shelf life of papain solutions.
Figure 7B:
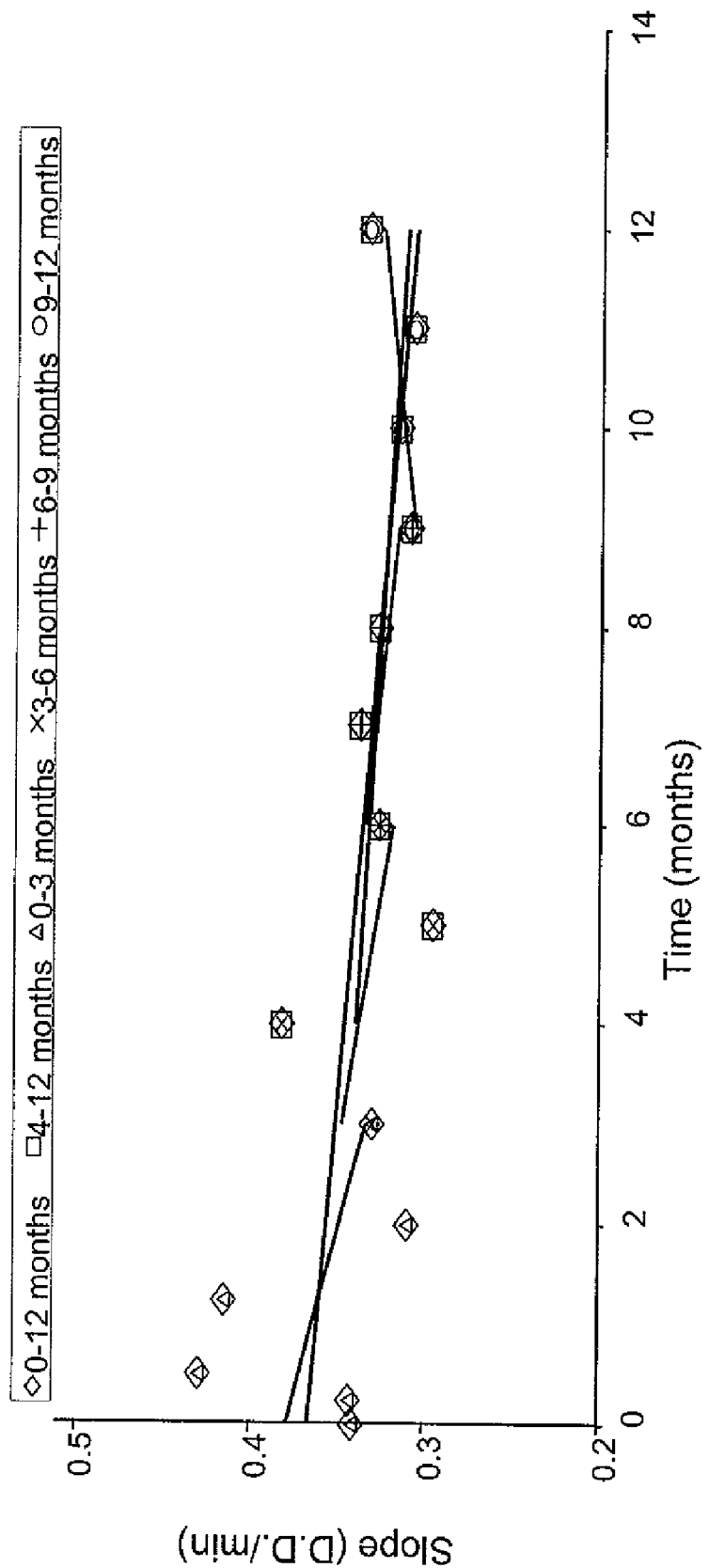

Results: As demonstrated by FIGS. 7A and 7B, an enzymatic composition comprising 30% Glycerol and 18% NaCl exhibits the highest residual enzymatic activity. Most, about 90%, of the initial slope of the enzymatic reaction was kept stable throughout 12 months of incubation at 4° C. Slope analysis (FIG. 7B) indicates faster decline in reaction kinetics during the first 3 months followed by stabilization of the residual activity, a phenomenon well documented for enzymes storage stability studies.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A composition comprising a non-active concentrate of a thiol-protease comprising at least 20 mg/ml of the inactive thiol protease and further comprising at least one osmotic agent, wherein said osmotic agent comprises glycerol and sodium chloride, and wherein the concentration of glycerol is at most 30% v/v and the concentration of sodium chloride is at most 18% w/v, and wherein said thiol-protease upon activation possesses proteolytic activity within the range of 5,000 to 50,000 USP units/mg.

2. The composition of claim 1, wherein the thiol protease is papain.

3. The composition of claim 1, wherein the concentration of the thiol protease is within the range of 25 to 45 mg/ml.

4. The composition of claim 1, wherein the non-active concentrate is devoid of particulate matter.

5. The composition of claim 1, wherein the non-active concentrate is stable under storage for at least one week at ambient temperatures, wherein upon activation said thiol-protease possesses proteolytic activity within the range of 5,000 to 50,000 USP units/mg.

6. The composition of claim 1, wherein the non-active concentrate is stable under storage in a temperature within the range of 4-10° C., wherein upon activation said thiol-protease possesses proteolytic activity within the range of 5,000 to 50,000 USP units/mg.

7. The composition of claim 1, further comprising a buffer, selected from the group consisting of: N-(2-Acetamido)-2-iminodiacetic acid buffer, acetate buffer, succinate buffer, maleate buffer, citrate buffer, MES buffer and combinations thereof, preferably acetate solution.

8. The composition of claim 1, wherein said composition is a dry concentrate.

9. A debriding solution comprising the concentrate of claim 1 diluted in at least one diluting solution, the at least one diluting solution comprising at least one reducing agent, buffer and at least one chelating agent, wherein the proteolytic activity of said thiol-protease in the debriding solution is within the range of 5,000 to 50,000 USP units/mg and wherein the debriding solution has a physiological pH.

10. The debriding solution of claim 9, wherein the at least one reducing agent is a thiol compound selected from the group consisting of: sulfide, cystamine, glutathione, N-acetyl cysteine, cysteine and cysteine hydrochloride.

11. The debriding solution of claim 9, wherein the buffer is selected from the group consisting of: tris hydroxymethylaminoethane (Tris) buffer, Hepes buffer, lysine buffer, glycine buffer, MOPS buffer, imidazole buffer and MES buffer.

12. The debriding solution of claim 9, wherein the at least one chelating agent is selected from the group consisting of: ethylenediaminetetracetic acid (EDTA), ethylene bis-(oxyethylene nitro) tetraacetic acid (EGTA) and ethylene dinitrilotetraacetic acid (Titriplex III).

13. A kit for preparing a debriding composition, the kit comprises a first component comprising a non-active concentrate of a thiol-protease comprising at least 20 mg/ml of the thiol protease and optionally comprising at least one osmotic agent, wherein said osmotic agent comprises glycerol and sodium chloride, and wherein the concentration of glycerol is at most 30% v/v and the concentration of sodium chloride is at most 18% w/v; a second component comprising a concentrated solution of at least one reducing agent; and a third component being a concentrated buffer solution comprising at least one buffering agent and at least one chelating agent, wherein mixing said first, second and third components in at least one diluting solution provides a debriding solution having a physiological pH and wherein said thiol-protease upon activation possesses proteolytic activity within the range of 5,000 to 50,000 USP units/mg.

14. The kit of claim 13, wherein the thiol protease is papain.

15. The kit of claim 13, wherein the first component is a solution having a pH within the range of pH 3-6.

16. The kit of claim 13, wherein the first component comprises a buffer selected from the group consisting of: acetate buffer, succinate buffer, maleate buffer, citrate buffer, MES buffer and combinations thereof.

17. The kit of claim 13, wherein the first component is stable under storage for at least one week at ambient temperatures.

18. The kit of claim 13, wherein the first component is stable under storage in a temperature within the range of 4-10° C.

19. The kit of claim 13, wherein the at least one reducing agent is a thiol compound selected from the group consisting of: sulfide, cystamine, gluthathione, N-acetyl cysteine, cysteine and cysteine hydrochloride.

20. The kit of claim 13, wherein the pH of the second component is within the range of pH 1 to 4.

21. The kit of claim 13, wherein the third component comprises a buffering agent selected from the group consisting of: tris hydroxymethylaminoethane (Tris) buffer, Hepes buffer, lysine buffer, glycine buffer, MOPS buffer, imidazole buffer and MES buffer.

22. The kit of claim 13, wherein following mixing of the first, second and third components and the at least one diluting solution, the buffering agent maintains a pH within the range of physiological pH.

23. The kit of claim 13, wherein the at least one diluting solution comprises a solution selected from the group consisting of: saline, hyperosmolaric saline and saline comprising at least one osmotic agent.

24. The kit of claim 13, wherein the volume ratio between each component of the kit independently and the volume of the debriding solution is at least 1:10.

25. The kit of claim 13, wherein the first component further comprises an inhibitor being capable of inhibiting the proteolytic activity of the said thiol-protease in a reversible manner.

26. A method for debriding a skin lesion or a damaged skin, the method comprising:
    (a) providing the kit of claim 13;
    (b) admixing the first, second and third components with the at least one diluting solution, thereby obtaining a debriding solution having a physiological pH, wherein the proteolytic activity of the said thiol-protease in said debriding solution is within the range of 5,000 to 50,000 USP units/mg;
    (c) applying the debriding solution onto the skin lesion or damaged skin; and, optionally,
    (d) covering said skin lesion with a dressing.

27. The method of claim 26, wherein the thiol protease is papain.

28. The method of claim 26, wherein the components of the kit are stable under storage for at least one weak under ambient conditions.

29. The method of claim 26, wherein step (c) comprises conveying a flow of the debriding solution through and over said skin lesion.

30. The method of claim 26, wherein the lesion is a chronic ulcer.

* * * * *